(12) United States Patent
Tsukada

(10) Patent No.: US 10,548,472 B2
(45) Date of Patent: Feb. 4, 2020

(54) OPHTHALMIC EXAMINATION SUPPORT SYSTEM, OPHTHALMIC EXAMINATION SUPPORT SERVER AND OPHTHALMIC EXAMINATION SUPPORT DEVICE

(71) Applicant: KABUSHIKI KAISHA TOPCON, Itabashi-ku (JP)

(72) Inventor: Hisashi Tsukada, Hachioji (JP)

(73) Assignee: KABUSHIKI KAISHA TOPCON, Itabashi-ku, Tokyo (JP)

( * ) Notice: Subject to any disclaimer, the term of this patent is extended or adjusted under 35 U.S.C. 154(b) by 151 days.

(21) Appl. No.: 15/574,856

(22) PCT Filed: Feb. 3, 2016

(86) PCT No.: PCT/JP2016/053277
§ 371 (c)(1),
(2) Date: Nov. 17, 2017

(87) PCT Pub. No.: WO2016/185736
PCT Pub. Date: Nov. 24, 2016

(65) Prior Publication Data
US 2018/0125351 A1 May 10, 2018

(30) Foreign Application Priority Data
May 20, 2015 (JP) .................. 2015-102383

(51) Int. Cl.
*A61B 3/00* (2006.01)
*A61B 3/02* (2006.01)
(Continued)

(52) U.S. Cl.
CPC .......... *A61B 3/0033* (2013.01); *A61B 3/0041* (2013.01); *A61B 3/0091* (2013.01);
(Continued)

(58) Field of Classification Search
CPC ... A61B 3/0033; A61B 3/0041; A61B 3/0091; A61B 3/10; A61B 3/02; A61B 3/102; A61B 3/14; A61B 3/0022; G16H 40/67
(Continued)

(56) References Cited

U.S. PATENT DOCUMENTS

| 5,911,687 A | 6/1999 | Sato et al. |
| 6,385,589 B1 * | 5/2002 | Trusheim .............. G06F 19/328 |
| | | 705/2 |

(Continued)

FOREIGN PATENT DOCUMENTS

| JP | H09-135816 A | 5/1997 |
| JP | 2002-083058 A | 3/2002 |

(Continued)

OTHER PUBLICATIONS

International Search Report dated Mar. 15, 2016 in connection with International Patent Application No. PCT/JP2016/053277, 3 pgs.

*Primary Examiner* — Collin X Beatty
(74) *Attorney, Agent, or Firm* — Chiesa Shahinian & Giantomasi PC

(57) ABSTRACT

An ophthalmic examination support system of an embodiment includes a server and clients. The server includes a medical information storage apparatus that stores medical information on each patient, and a management apparatus that manages the medical information. Each of the clients can communicate with the management apparatus. The system includes an association information storage unit and an examination condition obtaining unit. The association information storage unit stores, in advance, association information in which association between predetermined medical information items and examination conditions of an ophthalmic examination is recorded. The examination condition obtaining unit receives medical information retrieved from the medical information storage apparatus by the
(Continued)

management apparatus based on patient information transmitted from one of the clients, and obtains an examination condition corresponding to at least part of the received medical information from the association information. The client executes control based on the examination condition obtained.

16 Claims, 8 Drawing Sheets

(51) Int. Cl.
    *A61B 3/10*     (2006.01)
    *A61B 3/14*     (2006.01)
    *A61B 5/00*     (2006.01)

(52) U.S. Cl.
    CPC ............... *A61B 3/02* (2013.01); *A61B 3/102* (2013.01); *A61B 3/14* (2013.01); *A61B 5/0022* (2013.01)

(58) Field of Classification Search
    USPC ........................................................ 351/239
    See application file for complete search history.

(56) References Cited

U.S. PATENT DOCUMENTS

| | | | | |
|---|---|---|---|---|
| 7,756,309 | B2 * | 7/2010 | Gholap | G06F 16/58 |
| | | | | 382/128 |
| 8,620,678 | B2 * | 12/2013 | Gotlib | G06F 19/324 |
| | | | | 705/2 |
| 9,974,435 | B2 * | 5/2018 | Haddadi | G02C 13/005 |
| 10,242,443 | B2 * | 3/2019 | Hsieh | G06T 7/0012 |
| 2003/0074221 | A1 * | 4/2003 | Christ | G06F 19/3418 |
| | | | | 705/2 |
| 2003/0223038 | A1 * | 12/2003 | Alster | A61B 3/02 |
| | | | | 351/211 |
| 2004/0082845 | A1 | 4/2004 | Matsumoto et al. | |
| 2007/0162305 | A1 * | 7/2007 | Miller | G06Q 10/00 |
| | | | | 705/2 |
| 2009/0006131 | A1 | 1/2009 | Unger et al. | |
| 2011/0299034 | A1 | 12/2011 | Walsh et al. | |
| 2013/0172204 | A1 | 7/2013 | Grus et al. | |
| 2013/0215388 | A1 * | 8/2013 | Imamura | G06T 7/0012 |
| | | | | 351/206 |
| 2014/0129259 | A1 * | 5/2014 | Seriani | G06F 19/3418 |
| | | | | 705/3 |
| 2016/0071225 | A1 * | 3/2016 | Chmait | G06Q 20/102 |
| | | | | 705/2 |
| 2016/0198951 | A1 | 7/2016 | Fujimo et al. | |

FOREIGN PATENT DOCUMENTS

| | | |
|---|---|---|
| JP | 2004-154560 A | 6/2004 |
| JP | 2007-020563 A | 2/2007 |
| JP | 2009-011829 A | 1/2009 |
| JP | 2009-104278 A | 5/2009 |
| JP | 2010-193903 A | 9/2010 |
| JP | 2013-126422 A | 6/2013 |
| JP | 2013-529292 A | 7/2013 |
| JP | 2015-033471 A | 2/2015 |

* cited by examiner

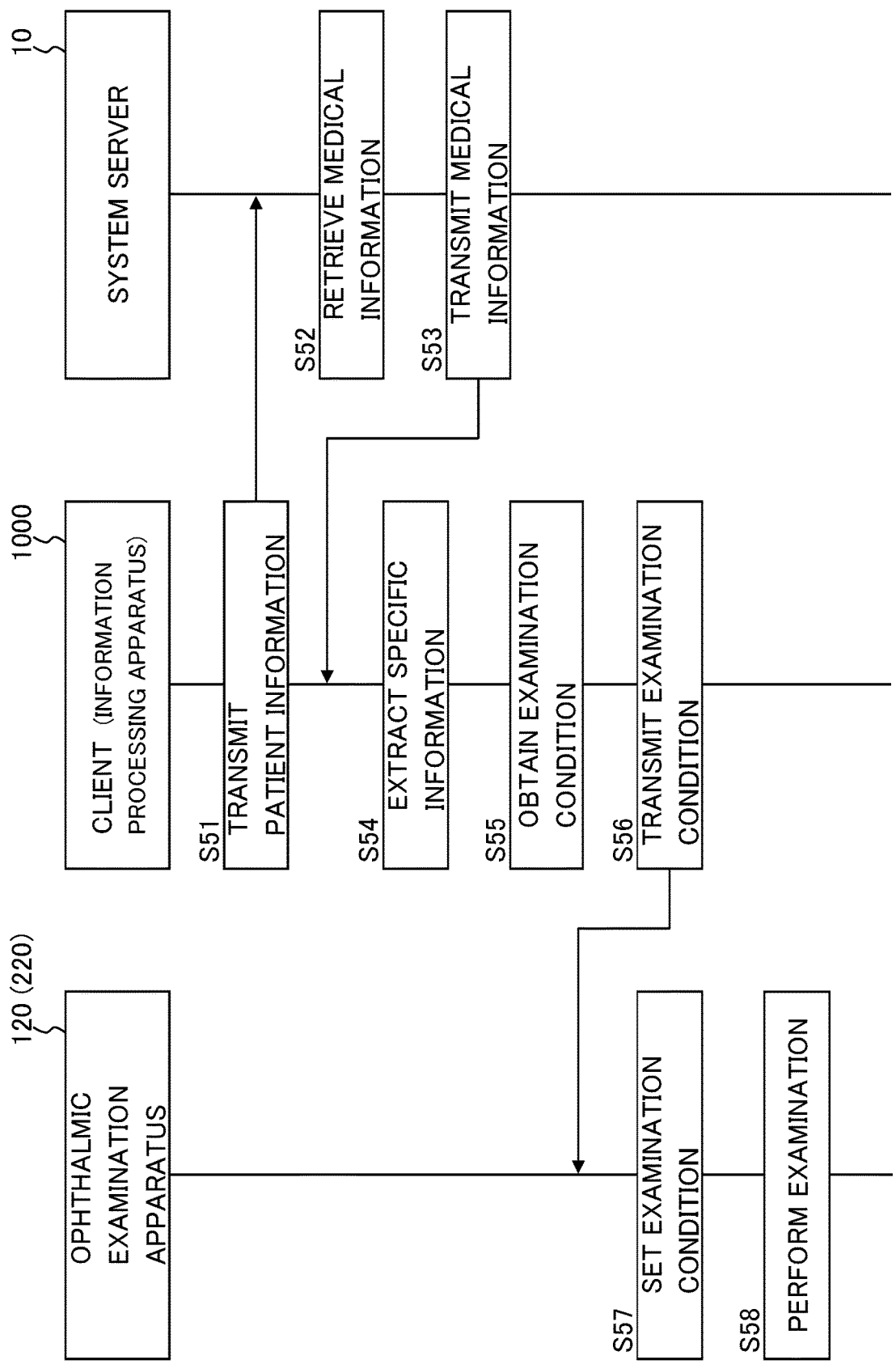

OPHTHALMIC EXAMINATION SUPPORT SYSTEM, OPHTHALMIC EXAMINATION SUPPORT SERVER AND OPHTHALMIC EXAMINATION SUPPORT DEVICE

CROSS-REFERENCE TO RELATED APPLICATIONS

This application is a national stage (under 35 U.S.C. 371) of International Patent Application No. PCT/JP2016/053277, filed Feb. 3, 2016, claiming priority to Japanese Patent Application No. 2015-102383, filed May 20, 2015, both of which are herein incorporated by reference in their entirety.

FIELD

Embodiments described herein relate generally to a system, a server, and a device for supporting an ophthalmic examination.

BACKGROUND

Various kinds of examination apparatuses are utilized in ophthalmology. Examples of such apparatuses include apparatuses for acquiring an image of a subject's eye (referred to as ophthalmic imaging apparatuses), and apparatuses for measuring a characteristic of a subject's eye (referred to as ophthalmic measurement apparatuses). Examples of the ophthalmic imaging apparatuses include optical coherence tomography apparatuses (OCT apparatuses for short), fundus cameras, slit lamp microscopes, and scanning laser ophthalmoscopes (SLOs for short). Examples of the ophthalmic measurement apparatuses include refractometers, keratometers, tonometers, and perimeters. In addition, multifunctional apparatuses that are configured to be capable of performing two or more kinds of examinations (e.g., imaging and/or measurements) are also used. Further, there also are ophthalmic examination apparatuses (e.g., ophthalmic imaging apparatuses, ophthalmic measurement apparatuses, and/or computers) that have a function of analyzing data acquired by imaging or measurement.

In recent years, early detection of disease, early treatment of disease, and preventive medicine attract attention, and research and development have been pursued for the improvement in examination accuracy for detecting slight symptoms and for establishing screening tests for estimating the possibility of the onset of disease before the appearance of symptoms. However, such advanced medical care is hardly provided in the present circumstances except for at advanced medical organizations such as university hospitals and core hospitals.

Meanwhile, a person who has become conscious of a symptom usually does not go to such an advanced medical organization but goes to a nearby clinic or the like. In addition, occasions for undergoing an examination before becoming conscious of a symptom are practically limited to standard medical check-up. Accordingly, although it is ideal to perform screening tests or the like, it is difficult to bring screening tests into practice in an effective and efficient manner.

Note that there are cases where a clinic or the like introduces a patient to another medical organization. In such a case, time, cost and physical burdens on the patient are large for the reason of carrying out similar examinations again, for example. One cause of such a problem is that systems for sharing electronic medical records and medical images among a plurality of medical organizations have not been established yet.

As described above, various kinds of examinations are carried out in the ophthalmology department. Further, in addition to unique examinations to ophthalmology, examinations common to other medical specialties (e.g., clinical examinations such as blood tests and biopsy) are also performed. There are differences in the kinds and the number of examinations that can be carried out between advanced medical organizations and other medical organizations. Hence, it is thought that the above problem is comparatively serious for ophthalmology.

Japanese Unexamined Patent Application Publication No. 2009-104278
Japanese Unexamined Patent Application Publication No. 2002-83058
Japanese Unexamined Patent Application Publication No. H09-135816
Japanese Unexamined Patent Application Publication No. 2013-126422
Japanese Unexamined Patent Application Publication (Translation of PCT Application) No. 2013-529292
Japanese Unexamined Patent Application Publication No. 2010-193903
Japanese Unexamined Patent Application Publication No. 2007-20563

SUMMARY

The purpose of the system, the server, and the device according to the present invention is to widely provide early detection methods, preventive medicine, or the like for eye disease.

An ophthalmic examination support system according to an embodiment include a server and a plurality of clients. The server includes a medical information storage apparatus configured to store medical information on each patient, and a management apparatus configured to manage the medical information stored in the medical information storage apparatus. The clients each is capable of communicating with the management apparatus. The ophthalmic examination support system according to the embodiment includes an association information storage unit and an examination condition obtaining unit. The association information storage unit is configured to store, in advance, association information in which association between predetermined medical information items and examination conditions of an ophthalmic examination is recorded. The examination condition obtaining unit is configured to receive medical information retrieved from the medical information storage apparatus by the management apparatus based on patient information transmitted from one of the plurality of clients, and to obtain an examination condition corresponding to at least part of the received medical information from the association information. The client executes control based on the examination condition obtained by the examination condition obtaining unit.

According to the present invention, it is possible to widely provide early detection methods, preventive medicine, or the like for eye disease.

BRIEF DESCRIPTION OF THE DRAWINGS

FIG. 8 is a sequence diagram showing an example of the usage mode of the ophthalmic examination support system of the embodiment.

DETAILED DESCRIPTION

Exemplary embodiments of an ophthalmic examination support system, an ophthalmic examination support server, and an ophthalmic examination support device will be described. The ophthalmic examination support system includes the ophthalmic examination support server and the ophthalmic examination support device. The contents of the documents cited in the present specification can be incorporated into embodiments of the present invention in an arbitrary manner.

<System Configuration>

Figure 1:
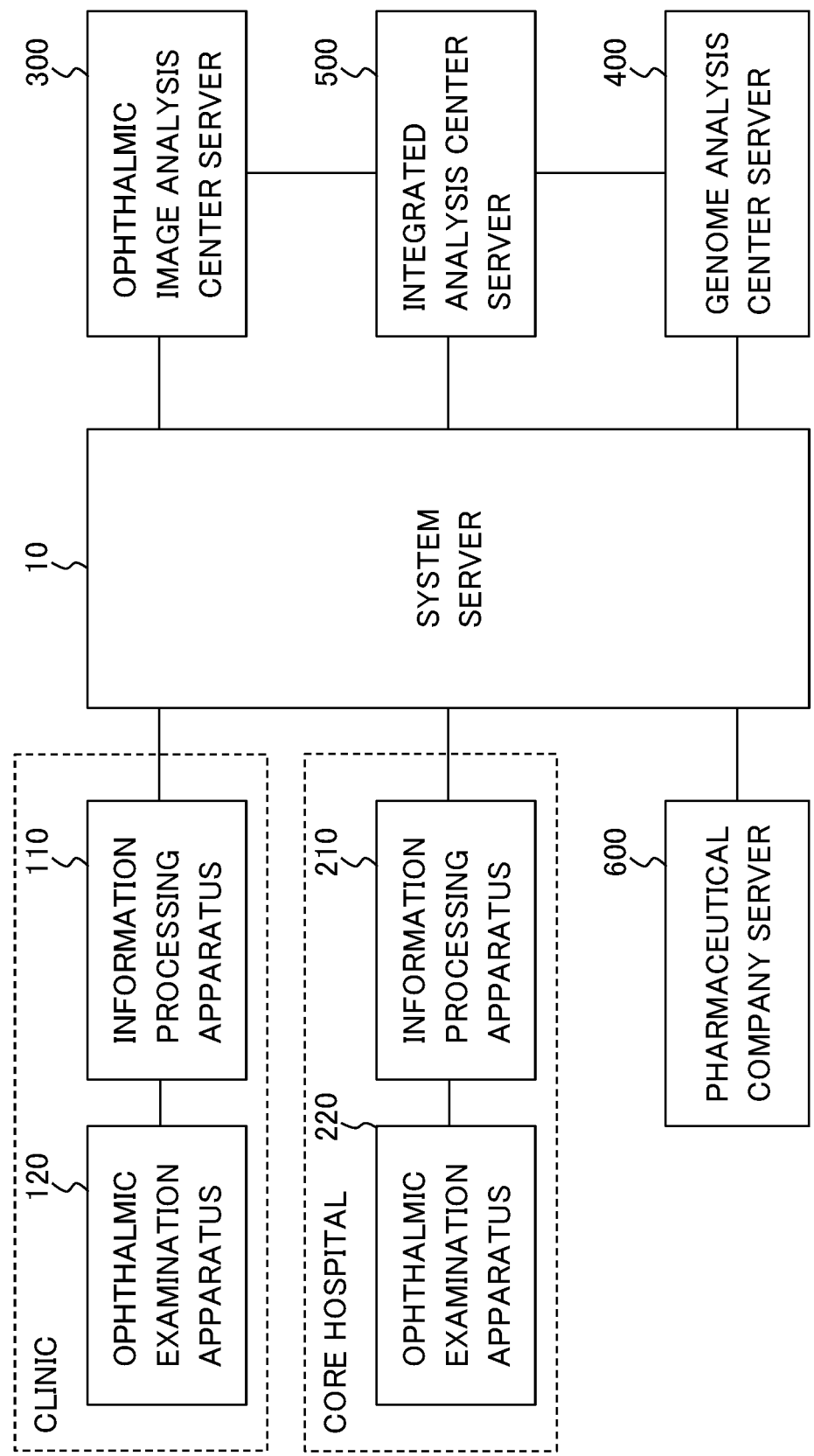
FIG. 1 is a schematic diagram showing an example of the configuration of the ophthalmic examination support system of the embodiment.
Figure 2:
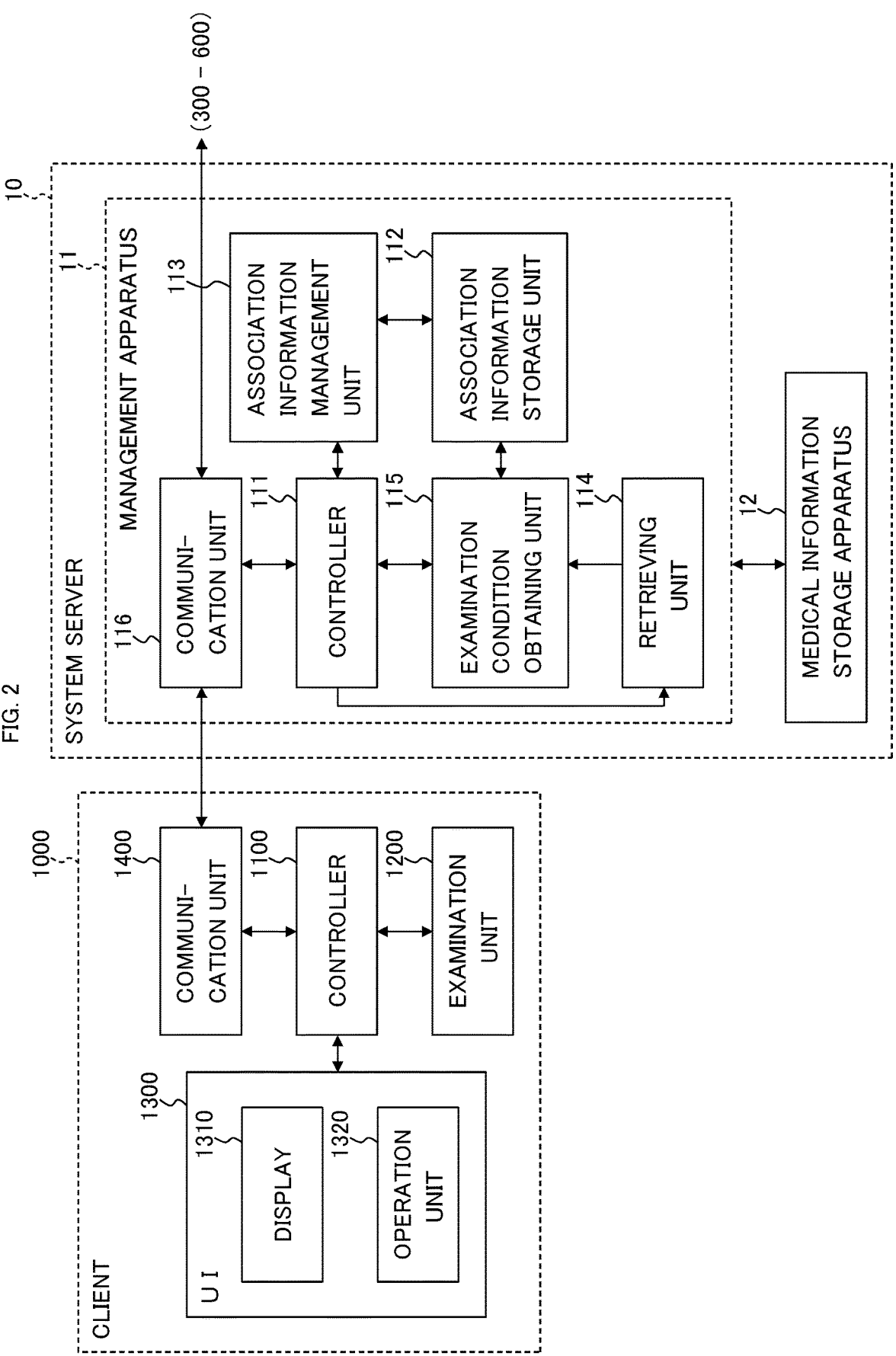
FIG. 2 is a schematic diagram showing an example of the configuration of the ophthalmic examination support system of the embodiment.

FIG. 1 and FIG. 2 show an example of the configuration of the ophthalmic examination support system according to the present embodiment. The ophthalmic examination system of the present embodiment includes part or all of the system shown in FIG. 1. FIG. 2 shows a configuration example of the system server 10 and the client 1000 included in the system shown in FIG. 1. The client 1000 includes an apparatus installed in a clinic or a core hospital. More specifically, the client 1000 may include the information processing apparatus 110 and/or the ophthalmic examination apparatus 120 installed in a clinic and may include the information processing apparatus 210 and/or the ophthalmic examination apparatus 220 installed in a core hospital.

The ophthalmic examination support system provides the service mainly with the system server 10. The service is provided to, for example, a plurality of clinics and a plurality of core hospitals. The system server 10 can communicate with the information processing apparatus 110 and/or the ophthalmic examination apparatus 120 installed in each clinic. Further, the system server 10 can communicate with the information processing apparatus 210 and/or the ophthalmic examination apparatus 220 installed in each core hospital.

Furthermore, the system server 10 can communicate, for example, with at least one of the following apparatuses:

an information processing apparatus installed in a facility for analyzing the results of an ophthalmic examination (e.g., the server 300 installed in an ophthalmic image analysis center for analyzing images of eyes, or the like);

an information processing apparatus installed in a facility for analyzing genetic information (e.g., the server 400 installed in a genome analysis center, or the like);

an information processing apparatus installed in a facility for analyzing the results of a plurality of ophthalmic examinations and the results of diagnoses performed by doctors, and the like in an integrated manner (e.g., the server 500 installed in an integrated analysis center for analyzing, in an integrated manner, medical information obtained at the clinics and the core hospitals, analysis results obtained at the ophthalmic image analysis center, and analysis results obtained at the genome analysis center, or the like);

an information processing apparatus installed in a company that provides a product to a medical institution or the like (e.g., the server 600 installed in a pharmaceutical company, a server installed in a medical device company, or the like).

Here, a clinic is a medical institution like a medical office that a patient consults a doctor first. At a clinic, for example, a general practitioner (a generalist) provides primary care. On the other hand, a core hospital is a medical institution that is the center of medical care in the relevant area. The core hospital is, for example, a large hospital or a university hospital that is capable of providing advanced medical care. According to the embodiment, kinds of medical institutions to which the service is provided is not limited to the above kinds, and may include any kinds of medical institutions. Further, the service may be provided not only to hospitals but also medical checkup centers, screening centers, or the like. In particular, the service according to the embodiment may include an information processing apparatus and/or an ophthalmic examination apparatus installed in an arbitrary facility. For example, it is possible to apply the configuration according to the embodiment to a case where the ophthalmic examination apparatus is installed at a patient's home or an elderly welfare facility for home medical care, or to a case where the ophthalmic examination apparatus is installed at a pharmacy or an optician's store for the wide area ophthalmic examination service. In the present embodiment, as a typical case, a system including a clinic and a core hospital will be described.

In addition, the information processing apparatus and the ophthalmic examination apparatus included in the ophthalmic examination support system are connected to at least the system server 10 via a communication line of an arbitrary form. The communication line of the embodiment includes a wide area network (WAN for short) such as the Internet or a dedicated line. Furthermore, the communication line of the embodiment may include an arbitrary kind of communication network such as a local area network like an in-hospital LAN constructed in a medical institution, a cable connecting a plurality of devices, a satellite communication network, and the like. At least part of the communication line of the embodiment may be wired, and at least part of the communication line of the embodiment may be wireless.

[Clinic]

In the clinic, the information processing apparatus 110 and the ophthalmic examination apparatus 120 are installed. The information processing apparatus 110 is an arbitrary kind of computer used in the clinic. The information processing apparatus 110 includes hardware such as a processor and a storage device, and software for executing various kinds of information processing (for example, information processing to be described later). The information processing apparatus 110 is, for example, a terminal used by a doctor (i.e., a doctor's terminal) or a server of an in-hospital LAN. The information processing apparatus 110 is a computer connected to the ophthalmic examination apparatus 120 via an in-hospital LAN, a cable, or the like. Alternatively, the information processing apparatus 110 may include a processor provided in the ophthalmic examination apparatus 120. Further, the information processing apparatus 110 may be a portable computer (e.g., a tablet, a notebook computer, or the like) usable outside the clinic, or may be a computer installed on a vehicle.

The ophthalmic examination apparatus 120 is used inside or outside the clinic. The ophthalmic examination apparatus 120 is an ophthalmic imaging apparatus and/or an ophthalmic measurement apparatus. Examples of the ophthalmic imaging apparatus include an OCT apparatus, a fundus camera, a slit lamp microscope, a SLO, and the like. Examples of the ophthalmic measurement apparatus include a refractometer, a keratometer, a tonometer, a perimeter, and the like. The ophthalmic examination apparatus 120 may be a multifunctional apparatus. Further, the ophthalmic examination apparatus 120 may have a function of analyzing data acquired through imaging or measurement. In the clinic, one or more ophthalmic examination apparatuses 120 are installed.

[Core Hospital]

In the core hospital, the information processing apparatus 210 and the ophthalmic examination apparatus 220 are installed. The information processing apparatus 210 and the ophthalmic examination apparatus 220 may be the same as the information processing apparatus 110 and the ophthalmic examination apparatus 120 installed in the clinic, respectively. The details of the apparatuses installed in the clinic and the details of the apparatuses installed in the core hospital will be described later.

[System Server 10]

The system server 10 is managed, for example, by a provider of the service according to the ophthalmic examination support system. The system server 10 includes hardware such as a processor and a storage device, and software for executing various kinds of information processing (for example, information processing to be described later). Details of the system server 10 will be described later.

[Ophthalmic Image Analysis Center Server 300]

The ophthalmic image analysis center is a facility that analyzes an image acquired by performing imaging of a patient's eye at a clinic or a core hospital. This analysis may include analysis using a computer (and an application program), analysis performed by a specialist, or the like. The ophthalmic image analysis center has a database constructed based on medical information such as the analysis results of ophthalmic images and the like.

The ophthalmic image analysis center server 300 may include one or more computers (e.g., processors) for analyzing an image of a patient's eye. Alternatively, the ophthalmic image analysis center server 300 may be connected to one or more such computers. The ophthalmic image analysis center server 300, for example, is equipped with the latest application programs for various kinds of analysis methods, and provides analysis with high precision and high accuracy. In addition, the ophthalmic image analysis center server 300 can provide an integrated analysis by combining a plurality of analysis application programs.

The ophthalmic image analysis center server 300 has, for example, a function of analyzing an image acquired by an OCT apparatus (an OCT image for short). Examples of the analysis of OCT images include the segmentation for determining a specific tissue or a tissue boundary of an eye, the size analysis for determining the size (e.g., the layer thickness, the area, the volume, or the like) of a specific tissue, and the like. Other examples of the kinds of the analysis that can be performed by the ophthalmic image analysis center server 300 are as follows: the optic disc analysis for determining an optic disc parameter such as the size, the shape (e.g., the inclination), or the like of an optic nerve head; the macula analysis for determining a macular parameter such as the shape of the macula, the layer thickness distribution, or the like; the lamina cribrosa analysis for determining a lamina cribrosa parameter such as the thickness, the shape, the distribution of pores of the lamina cribrosa, or the like; the analysis of blood vessel and blood flow for determining a blood vessel parameter or a blood flow parameter such as the distribution of fundus blood vessels, the blood flow dynamics, or the like; the cornea analysis for determining a cornea parameter such as the shape (e.g., the curvature, or the like), the layer thickness distribution of the cornea, or the like; the corner angle analysis for determining a corner angle parameter such as the angle of the corner angle (also referred to as the angulus iridocornealis) that is the intersection position of the cornea and the iris; the transplant analysis for determining an evaluation parameter relating to an intraocular lens, a cell sheet, or the like implanted in a patient's eye. The details of the processing executed by the ophthalmic image analysis center server 300 will be described later.

[Genome Analysis Center Server 400]

The genome analysis center is a facility that performs genetic tests on specimens collected from a patient (e.g., blood, extracted tissue, saliva, urine, hair, spermatozoon, ovum, or the like). In addition, the genome analysis center has a database constructed based on medical information such as the results of genetic tests.

The genome analysis center may be capable of performing full genome (or whole genome) analysis to obtain whole genetic information of a patient. Further, the genome analysis center may be capable of performing a pseudo full genome analysis that obtains a pseudo whole genetic information of a patient by referring to statistical data of a large number of pieces of full genome information. In addition, the genome analysis center may be able to determine the risk of a specific disease or the like from the genetic information of a patient.

The genome analysis center server 400 may include one or more computers (e.g., processors) for analyzing genetic information of a patient. Alternatively, the genome analysis center server 400 may be connected to one or more such computers. The genome analysis center server 400, for example, is equipped with the latest application programs for various kinds of analysis methods, and provides analysis with high precision and high accuracy. In addition, the genome analysis center server 400 can provide an integrated analysis by combining a plurality of analysis application programs.

[Integrated Analysis Center Server 500]

The integrated analysis center is a facility that analyzes results of various tests, diagnoses, and the like in an integrated manner. This analysis may include analysis using a computer (and an application program), analysis performed by a specialist, or the like. The integrated analysis center has a database constructed based on medical information such as various kinds of test results, diagnosis results, or the like. In the present embodiment, an integrated analysis including at least the analysis result of an ophthalmic image obtained at the ophthalmic image analysis center and the result of a genetic test obtained at the genome analysis center is performed. In addition, the result of diagnosis obtained at a clinic, a core hospital, or the like may be taken into account.

The integrated analysis center server 500 may include one or more computers (e.g., processors) for performing integrated analysis of a patient's eye. Alternatively, the integrated analysis center server 500 may be connected to one or more such computers. The integrated analysis center server 500, for example, is equipped with the latest application programs for various kinds of analysis methods, and provides analysis with high precision and high accuracy.

[Pharmaceutical Company Server 600]

The pharmaceutical company uses the data accumulated by the ophthalmic examination support system (or the information processing apparatus connected thereto) for drug discovery research. The pharmaceutical company server 600 receives such accumulated data from the system server 10 or other information processing apparatus (e.g., the ophthalmic image analysis center server 300, the genome analysis center server 400, the integrated analysis center server 500, or the like).

<Configurations of the System Server 10 and the Client 1000>

The system server 10 and the client 1000 will be described with reference to FIG. 2.

[Client 1000]

As mentioned above, the client 1000 includes one or more apparatuses installed in a clinic or a core hospital. For example, the client 1000 installed in a clinic includes the information processing apparatus 110 and/or the ophthalmic examination apparatus 120. Similarly, the client 1000 installed in a core hospital includes the information processing apparatus 210 and/or the ophthalmic examination apparatus 220.

The client 1000 includes the controller 1100, the examination unit 1200, the user interface unit (UI unit for short) 1300, and the communication unit 1400.

(Controller 1100)

The controller 1100 includes a processor and controls each part of the client 1000. For example, the controller 1100 controls the examination unit 1200 to perform examination on a patient's eye. The control of the examination unit 1200 includes control to set an examination condition.

(Examination Unit 1200)

The examination unit 1200 performs examination of the patient's eye under the control of the controller 1100. The examination unit 1200 includes, for example, the ophthalmic examination apparatus 120 or the ophthalmic examination apparatus 220.

In the case where the examination unit 1200 has an imaging function, the examination unit 1200 includes, for example, an optical system for projecting light onto a patient's eye and an optical system for detecting returning light of the light projected onto the patient's eye. In addition, the examination unit 1200 may include other optical systems, such as an optical system for projecting a fixation target onto the patient's eye. Further, the examination unit 1200 may include a processor for processing a detection result of the returning light (e.g., an image signal, a video signal, or the like).

OCT is an example of the imaging function. An OCT optical system is configured to split light from a light source into measurement light and reference light, generate interference light by superposing the returning light of the measurement light from the patient's eye and the reference light, and detect the interference light. In addition, a processor and the like that forms image data by applying signal processing such as fast Fourier transform (FFT) and the like to the detection result of the interference light is provided. The optical path of the measurement light (referred to as the measurement arm or sample arm) includes various kinds of members such as an optical scanner for scanning the patient's eye with the measurement light, a focusing lens for changing the focus position of the measurement light, an optical path length changing mechanism (e.g., a corner tube or the like) for changing the length of the measurement arm, and the like. The optical path of the reference light (referred to as the reference arm) includes various kinds of members such as a polarization controller, an optical attenuator, an optical path length changing mechanism (e.g., a reference mirror, a mechanism for moving the reference mirror, or the like), and the like. The examination conditions for OCT include the followings: the fixation position (e.g., the control condition of the fixation target projection optical system); the light amount/wavelength (e.g., the control condition of the light source); the scanning pattern with the measurement light (e.g., the control condition of the optical scanner); the focus position (e.g., the control conditions of the focusing lens); the optical path length of the measurement arm and/or the optical path length of the reference arm (e.g., the control condition of the optical path length changing mechanism); the polarization adjustment state (e.g., the control condition of the polarization controller), the optical attenuation state (e.g., the control condition of the optical attenuator). Further, in the case where the function of analyzing OCT images is performed by the examination unit 1200, the examination conditions may include a parameter for the analysis processing.

The examination conditions such as the fixation position, the light amount/wavelength, the scanning pattern, the focus position, or the like are applied to the case of SLO in a similar manner. In addition, the examination conditions such as the fixation position, the light amount/wavelength, the focus position, or the like are applied to the case of fundus camera in a similar manner. In the case where the examination unit 1200 includes an OCT apparatus, an SLO, a fundus camera, or the like, alignment that is position adjustment of the optical system with respect to the patient's eye and focusing of the optical system with respect to the fundus are carried out. These are performed based on an indicator projected on the patient's eye. A parameter relating to the alignment or the focusing can be employed as an examination condition. In the case where the examination unit 1200 includes a slit lamp microscope, the position (or the angle) of an illumination optical system, the position (or the angle) of an imaging optical system, the slit width, or the like can be applied to the examination condition in addition to the light amount/wavelength.

In the case where the examination unit 1200 has a measurement function, the examination unit 1200 includes, for example, an optical system for projecting light onto a patient's eye and an optical system for detecting returning light of the light projected onto the patient's eye. In addition, the examination unit 1200 may include other optical systems, such as an optical system for projecting a fixation target on the patient's eye. Further, the examination unit 1200 may include a processor for processing a detection result of the returning light (e.g., an image signal, a video signal, or the like). Examples of the measurement function include, for example, the eye refractive power measurement function (e.g., a refractometer), the corneal shape measurement function (e.g., a keratometer), the intraocular pressure measurement function (e.g., a tonometer), the visual field test function (e.g., a perimeter), and the like. The examination unit 1200 has a configuration according to the measurement function installed on it, and an examination condition according to the configuration is applied.

(User Interface Unit 1300)

The user interface unit 1300 includes the display 1310 and the operation unit 1320. The display 1310 includes a display device provided in the information processing apparatus 110

(or 210), a display device provided in the ophthalmic examination apparatus 120 (or 220), or the like. The operation unit 1320 includes a keyboard, a mouse, or the like provided in the information processing apparatus 110 (or 210), a button, a joystick, a knob, or the like provided in the ophthalmic examination apparatus 120 (or 220), an operation attachment connected to the ophthalmic examination apparatus 120 (or 220), or the like. The display 1310 and the operation unit 1320 do not need to be configured as separate devices. The display 1310 and the operation unit 1320 may be a device like a touch panel in which the display function and the operation function are integrated.

(Communication Unit 1400)

The communication unit 1400 includes a communication interface for communicating with an external device such as the system server 10. The communication interface has a configuration conforming to a network standard applied to the ophthalmic examination support system.

[System Server 10]

The system server 10 includes the management apparatus 11 and the medical information storage apparatus 12. Note that the system server 10 may be constructed as a server on the network (for example, a cloud server), or may be installed in a core hospital or the like. Alternatively, a similar configuration to the system server 10 (for example, a cloud server) arranged on the network may be provided in the core hospital. Further, a combination of a first server arranged on a network (for example, a cloud server) and a second server provided in a core hospital may be configured to provide the functions of the system server 10.

(Medical Information Storage Apparatus 12)

The medical information storage apparatus 12 includes one or more large-capacity storage devices such as a hard disk drive and stores medical information on each patient. Identification information is assigned to each patient. In the medical information storage apparatus 12, for example, the accounts for the respective patients are provided. Alternatively, in the medical information storage apparatus 12, the storage areas (e.g., the folders) for the respective patients are provided. Medical information includes various kinds of data relating to a patient or a patient's eye such as an image (e.g., an OCT image, an SLO image, a fundus front image, a slit cross sectional image, or the like), a feature value (e.g., refractive power, corneal curvature, intraocular pressure, or the like), image analysis data, characteristic analysis data, genetic information (and/or analysis data of genetic information), a result of diagnosis (e.g., a diagnostic report), a result of interpretation (e.g., an interpretation report), a result of specimen examination (e.g., a specimen examination report), or the like.

(Management Apparatus 11)

The management apparatus 11 performs the management of the medical information stored in the medical information storage apparatus 12. The management apparatus 11 includes the controller 111, the association information storage unit 112, the association information management unit 113, the retrieving unit 114, the examination condition obtaining unit 115, and the communication unit 116.

(Controller 111)

The controller 111 includes a processor and controls each part of the management apparatus 11 (i.e., the system server 10).

(Association Information Storage Unit 112)

The association information storage unit 112 stores, in advance, association information in which predetermined medical information items and examination conditions of an ophthalmic examination are associated with one another.

The medical information items included in the association information are selected according to the types of ophthalmic examinations, examination conditions, or the like. Examples of the medical information items include items included in image analysis data, items included in characteristic analysis data, items included in genetic information (and/or items included in analysis data of genetic information), items included in results of diagnoses, items included in interpretation result, items included in specimen examination results, and the like. Specific examples of the medical information items include a parameter indicating the thickness (or the thickness distribution) of a predetermined layer of a retina, a parameter indicating the shape of an optic nerve head, a parameter indicating the defect state of a retinal nerve fiber layer (RNFL for short), a parameter indicating the bleeding state in the vicinity of an optic nerve head, a parameter indicating the atrophy state of a choroid around an optic nerve head, and the like. These items relate to glaucoma. Examples of items relating to age-related macular degeneration include a parameter indicating the state of new blood vessels extending from a choroid toward a retinal surface, a parameter indicating the distribution of drusens, a parameter indicating the detachment state of a retinal pigment epithelium (RPE for short), a parameter indicating the state of submacular hemorrhage, and the like. These parameters are acquired by analytical processing using a computer, interpretation or diagnosis by a specialist, or the like. In addition, character string information (e.g., the name of disease, the findings, the name of medication administered, the numerical values, or the like) included in interpretation reports, diagnostic reports, specimen examination reports, or the like can also be used as medical information items. Further, characteristic items obtained from image information (e.g., schemata or the like) can also be used as medical information items.

The examination conditions included in the association information do not only include the various kinds of parameters as described above but may also include the followings: an examination type (and/or analysis type); a combination of a plurality of examination types (and/or analysis types) (e.g., examination menu/analysis menu); a type of a computer program for performing one or more examinations (and/or analysis types), or the like. Examples thereof include one or more examination types relating to a specific disease (e.g., glaucoma, age-related macular degeneration, diabetic retinopathy, or the like), one or more analysis types relating to a specific disease, a type of a computer program for performing such an examination and/or such analysis, and the like.

Several examples of the association information will be described. The association information storage unit 112 may store at least one of the first association information and the second association information described below.

In the first association information, related genetic information of a predetermined disease and examination conditions of the ophthalmic examination relating to the predetermined disease are associated with one another. For example, the first association information may include association between information indicating genes relating to the risk of onset of glaucoma and examination conditions of an ophthalmic examination relating to glaucoma (e.g., three dimensional OCT scan, peripapillary OCT scan, fundus imaging (or fundus photography), RNFL analysis, optic nerve head shape analysis, lamina cribrosa analysis, or the like). Furthermore, the first association information may include association between information indicating genes relating to the risk of onset of age-related macular degeneration and examination conditions of an ophthalmic examination relating to age-related macular degeneration (e.g., macular three dimensional OCT scan, fundus imaging (or fundus photography), drusen analysis, RPE analysis, or the like).

In the second association information, feature information indicating morphological features and/or functional features of eyes suffering from a predetermined disease and examination conditions of an ophthalmic examination relating to the predetermined disease are associated with one another. The morphological features are visually identifiable features such as the shape, size, placement and color of a site of an eye (e.g., the eye fundus, the anterior eye segment, or the like). The morphological features are determined from an image, for example. As a specific example, a feature relating to the optic nerve head (e.g., C/D ratio, R/D ratio, size, or the like), lesion (e.g., drusen, bleeding, new blood vessels, or the like), bleeding, new blood vessels, or the like is determined from a front image acquired by an OCT apparatus, a fundus camera, an SLO, or the like. Also, a feature relating to the optic nerve head (e.g., cross sectional shape, inclination, size, or the like), macula (e.g., cross sectional shape or the like), lesion (e.g., drusen, edema, or the like), layer thickness, layer defect, or the like is determined from a cross sectional image (e.g., a B scan image, a three dimensional image, or the like) acquired by an OCT apparatus. The functional features are features relating to functions as a living tissue. Examples thereof include features of blood flow dynamics (e.g., blood flow amount, blood flow velocity, or the like) in a fundus blood vessel, features of liquid circulation dynamics in an eye, and the like.

For example, the second association information may include association between information indicating morphological features of glaucomatous eyes (e.g., a threshold value of the peripapillary RNFL thickness, a threshold value of the papillary rim thickness, or the like) and examination conditions of an ophthalmic examination relating to glaucoma (e.g., three dimensional OCT scan, peripapillary OCT scan, fundus imaging (or fundus photography), RNFL analysis, optic nerve head shape analysis, lamina cribrosa analysis, or the like). Further, the second association information may include association between information indicating morphological features of age-related macular degeneration (e.g. drusen distribution, RPE detachment, or the like) and examination conditions of an ophthalmic examination relating to age-related macular degeneration (e.g., macular three dimensional OCT scan, fundus imaging (or fundus photography), drusen analysis, RPE analysis, or the like).

(Association Information Management Unit 113)

The association information management unit 113 manages the association information. For example, the association information management unit 113 performs the update of the association information. Examples of the update processing will be described below. The update processing is executed at an arbitrary timing. For example, it is possible to execute update processing on a regular basis. Alternatively, the update processing can be executed in response to an instruction from a doctor, an administrator, or the like. Further, it is possible to execute the update processing according to the state of accumulation of medical information.

In the case where the first example of the update processing is applied, the client 1000 transmits medical information including the examination data of the patient's eye obtained by the examination unit 1200 (e.g., an image, an examination result, a result of diagnosis, or the like), together with the patient information (e.g., patient identification information or the like), to the management apparatus 11. The controller 111 stores the medical information transmitted from the client 1000 in the medical information storage apparatus 12. The association information management unit 113 updates the association information by applying statistical processing to the medical information of a plurality of patients stored in the medical information storage apparatus 12.

Here, the update processing is executed as follows, for example. First, the association information management unit 113 selectively acquires medical information relating to the association information to be updated from the medical information storage apparatus 12. This selection process includes, for example, a retrieving process using an examination condition and a medical information item included in the association information as a query. With this, medical information including a concerned item and a concerned examination condition is acquired. Next, the association information management unit 113 extracts information on the concerned item and information on the concerned examination condition from the acquired medical information. Subsequently, the association information management unit 113 determines a statistical relationship between the extracted information on the concerned item and the extracted information on the concerned examination condition. This processing includes a process of determining a statistical value such as the average, dispersion (e.g., standard deviation, variance), median, mode, maximum value, minimum value, or the like. Further, the processing may also include a process of determining the correlation between both parameters. Also, this statistical processing may be executed by taking into account information included in the current association information or information used for generating the current association information. In this way, new association information about the concerned item and the concerned examination condition is generated, and the current association information is replaced with the new association information. Such a series of processes is executed for each piece of association information.

Also in the case where the second example of the update processing is applied, the client 1000 transmits medical information including the examination data of the patient's eye obtained by the examination unit 1200 (e.g., an image, an examination result, a result of diagnosis, or the like), together with the patient information (e.g., patient identification information or the like), to the management apparatus 11. The controller 111 transmits the inputted examination data (e.g., the image or the like) to a computer installed in an examination data analysis organization (e.g., to the ophthalmic image analysis center server 300 or the like). The analysis result of the examination data is inputted to the management apparatus 11 and stored in the medical information storage apparatus 12. The association information management unit 113 updates the association information by executing statistical processing of the medical information (including the analysis results of examination data) of a plurality of patients stored in the medical information storage apparatus 12. This statistical processing may be executed in the same manner as in the first example.

(Retrieving Unit 114)

The retrieving unit 114 retrieves medical information from the medical information storage apparatus 12 based on the patient information inputted from the client 1000. As described above, the medical information storage apparatus 12 stores medical information for each patient. The patient information inputted from the client 1000 includes identification information of the patient. The retrieving unit 114 retrieves medical information using the patient identification information as a query.

(Examination Condition Obtaining Unit 115)

The examination condition obtaining unit 115 receives the medical information retrieved by the retrieving unit 114 and obtains an examination condition(s) corresponding to at least part of the medical information from the association information.

The association information associates predetermined medical information items and examination conditions with each other. As for each medical information inputted from the retrieving unit 114, the examination condition obtaining unit 115 first determines whether or not this medical information corresponds to a predetermined item. This processing is carried out, for example, by determining whether the item indicated by this medical information is included in the association information. In other words, this processing is executed by determining whether or not the item indicated by this medical information corresponds to any of the predetermined items. As a result, medical information corresponding to a predetermined item is extracted from the medical information retrieved by the retrieving unit 114.

Subsequently, the examination condition obtaining unit 115 obtains the examination condition associated with the extracted medical information from the association information. Several examples of the processing executed by the examination condition obtaining unit 115 will be described below.

The first example will be described. In the present example, the above-mentioned first association information is referred to. The first association information records the association between related genetic information of a predetermined disease and examination conditions of an ophthalmic examination relating to the predetermined disease. The examination condition obtaining unit 115 first extracts genetic information from the medical information retrieved by the retrieving unit 114. In the case where the medical information does not include genetic information, the processing according to the present example is not executed.

In the case where the genetic information is included in the medical information, the examination condition obtaining unit 115 determines whether or not this genetic information includes any of the related genetic information included in the first association information. This determination process is executed by, for example, searching the genetic information (e.g., gene sequence or the like) of the patient to determine whether the gene relating to the risk of onset of a specific disease (for example, glaucoma) is included. Alternatively, this determination process is executed by searching within an examination report included in the genetic information of the patient to determine whether the information (e.g., a character string or the like) indicating a specific disease is included.

In the case where it is determined that the genetic information of the patient does not include any related genetic information, the processing according to the present example ends here. On the other hand, in the case where it is determined that the genetic information of the patient includes some of the related genetic information included in the first association information, the examination condition obtaining unit 115 acquires the examination condition corresponding to the related genetic information from the first association information. With this, an examination condition(s) corresponding to the related gene of the specific disease is selected.

The selected examination condition includes one or more examination types (and/or one or more analysis types) for carrying out diagnosis on the disease, an examination parameter, a type of computer program for examination, or the like. When the type of the computer program is acquired, the examination condition obtaining unit 115 can acquire the computer program of the type (e.g., an examination application program, an analysis application program, or the like) from a program storage unit (not shown). The acquired computer program is transmitted to the client 1000 for installation. In the case where various kinds of application programs are installed in the client 1000 in advance, it is not necessary to execute the acquisition and the transmission of the computer program, and it is sufficient to transmit, to the client 1000, information indicating the type of the computer program acquired from the first association information.

A second example will be described. In the present example, the above-mentioned second association information is referred to. The second association information records the association between feature information indicating morphological features and/or functional features of eyes suffering from a predetermined disease and examination conditions of an ophthalmic examination relating to the predetermined disease. The examination condition obtaining unit 115 first extracts an image of the patient's eye from the medical information retrieved by the retrieving unit 114. In the case where the medical information does not include an image, the processing according to the present example is not executed.

In the case where the medical information includes an image, the examination condition obtaining unit 115 analyzes the image to determine whether or not the image indicates any of the morphological features and/or the functional features indicated in the second association information. For example, this determination process includes an image analysis for specifying an image region corresponding to a specific site of the patient's eye (for example, segmentation), and image processing for obtaining morphology information (e.g., shape, size, arrangement, or the like) of the specified image region. Further, this determination process may include image processing for obtaining function information such as fundus blood flow.

Subsequently, the examination condition obtaining unit 115 obtains, from the second association information, the examination condition corresponding to the feature information indicating the morphological feature and/or the functional feature determined to be included in the image. With this, the examination condition corresponding to the disease specified from the morphological feature and the functional feature of the patient's eye is selected. The examination condition to be selected is the same as in the first example.

Note that there are cases where a site depicted in an image included in the medical information can be specified without executing the analysis of the image. For example, there is a case where information indicating a target site of imaging (e.g., fixation position information or the like) is attached to an image. The same applies to the case where a target site of imaging can be specified from other information included in the medical information (e.g., the name of the site, disease name, schema, or the like recorded in the diagnosis report or interpretation report). In such a case, the examination condition obtaining unit 115 can select one or more images from a plurality of images included in the medical information and execute the above processing on the selected images. In addition, it is also possible to select an image which particularly attracts attention in the interpretation report or the like and execute the above processing on the selected image.

A third example will be described. In the second example, the examination condition obtaining unit 115 executes an image analysis. In the present example, an image analysis data received from the ophthalmic image analysis center server 300 or the like is referred to. Further, in the present example, the second association information is referred to as in the second example.

The examination condition obtaining unit 115 first extracts image analysis data of the patient's eye from the medical information retrieved by the retrieving unit 114. In the case where the medical information does not include image analysis data, the processing according to the present example is not executed.

In the case where the medical information includes image analysis data, the examination condition obtaining unit 115 determines whether this image analysis data corresponds to any of the morphological features and/or the functional features indicated in the second association information. This determination process is executed, for example, by searching within the image analysis data for information (e.g., a character string, a numerical value, or the like) corresponding to the morphological features and/or the functional features indicated in the second association information.

Subsequently, the examination condition obtaining unit 115 obtains, from the second association information, the examination condition corresponding to the feature information indicating the morphological feature and/or the functional feature determined to correspond to the image analysis data.

In the second and third examples, the image of the patient's eye may be an OCT image. OCT images are high definition, and can not only depict the surface but also the deep part of the tissues. Thus, OCT images are effective for early detection of disease.

(Communication Unit 116)

The communication unit 116 includes a communication interface for communicating with external devices such as the client 1000, the ophthalmic image analysis center server 300, the genome analysis center server 400, the integrated analysis center server 500, the pharmaceutical company server 600, and the like. The communication interface has a configuration conforming to the network standard applied to the ophthalmic examination support system.

In this specification, the term "processor" is used to mean, for example, a circuit such as a central processing unit (CPU), a graphics processing unit (GPU), an application specific integrated circuit (ASIC), a programmable logic device (for example, a simple programmable logic device (SPLD), a complex programmable logic device (CPLD), or a field programmable gate array (FPGA)), or the like. The processor realizes the functions according to the embodiment, for example, by reading our and executing a program stored in a storage circuit or a storage device. At least part of the storage circuit or at least part of the storage device may be included in the processor.

<Usage Mode>

Several examples of the usage mode of the ophthalmic examination support system according to the present embodiment will be described.

[Usage Mode 1]

Figure 3:
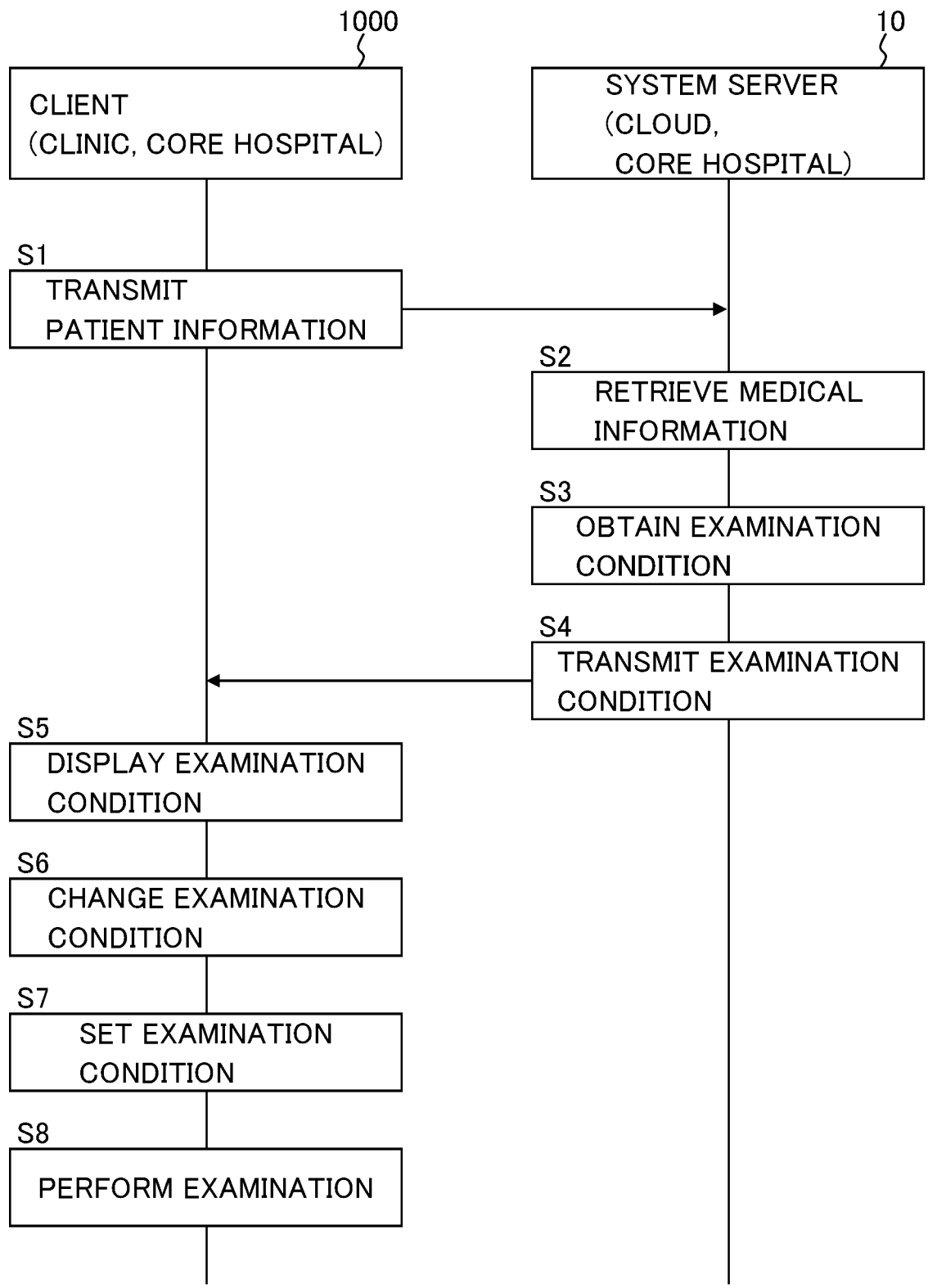
FIG. 3 is a sequence diagram showing an example of the usage mode of the ophthalmic examination support system of the embodiment.

The first usage mode is shown in FIG. 3.

(S1: Transmit Patient Information)

A user (e.g., a doctor, a paramedic, or the like) of the client 1000 inputs patient information of a patient to the client 1000. The patient information includes, for example, a patient ID in the clinic and/or patient identification information used in the present system. In the case where only the patient ID is included, the client 1000 or the system server 10, which has stored in advance information indicating the correspondence relationship between a plurality of pieces of patient ID and a plurality of pieces of patient identification information (e.g., table information or the like), specifies the patient identification information corresponding to the patient ID at a certain stage.

Patient information is entered in an arbitrary way. For example, patient information is manually entered using a keyboard or a graphical user interface (GUI for short). Alternatively, patient information can be read from a patient card (e.g., an IC card, a magnetic card, or the like). It is also possible to input patient information using biometric information (e.g., fingerprint, iris pattern, or the like).

Under the control of the controller 1100, the communication unit 1400 transmits at least the patient identification information (or the patient ID) of the inputted patient information to the management apparatus 11. At this time, identification information of the client 1000 (or, identification information of the facility in which the client 1000 is installed, or that of the user of the client 1000) is also transmitted together with the patient information.

(S2: Retrieve Medical Information)

The communication unit 116 of the management apparatus 11 receives the patient information transmitted from the client 1000 in step S1 and sends it to the controller 111. The controller 111 sends the patient identification information included in the patient information to the retrieving unit 114. The retrieving unit 114 acquires, from the medical information storage apparatus 12, medical information corresponding to the patient identification information inputted from the controller 111. The retrieving unit 114 sends the acquired medical information to the examination condition obtaining unit 115.

(S3: Obtain Examination Condition)

The examination condition obtaining unit 115 obtains the examination condition(s) corresponding to at least part of the medical information inputted from the retrieving unit 114 in step S2, from the association information stored in the association information storage unit 112. Then, the examination condition obtaining unit 115 sends the obtained examination condition to the controller 111.

(S4: Transmit Examination Condition)

The controller 111 controls the communication unit 116 so that the examination condition inputted from the examination condition obtaining unit 115 in step S3 is transmitted to the client 1000 from which the patient information has been transmitted (here, such a client 1000 is referred to as a transmission source).

It should be noted that the transmission source of the patient information and the transmission destination of the examination condition may be different. In that case, the transmission destination of the examination condition is set in advance. Alternatively, the transmission destination of the examination condition is set each time using the client 1000 or the like.

(S5: Display Examination Condition)

The communication unit 1400 of the client 1000 receives the examination condition transmitted from the management apparatus 11 in step S4 and sends it to the controller 1100. The controller 1100 displays the examination condition on the display 1310. At this time, a predetermined screen (e.g., GUI) is displayed on the display 1310, and the examination condition is presented on the screen.

(S6: Change Examination Condition)

The user of the client 1000 checks the examination condition displayed in step S5. In case where the user wishes to change (e.g. correct, add, delete, or the like) the examination condition, the user performs an operation for the change using the operation unit 1320. The controller 1100 saves the contents of the change made by the user together with the examination condition inputted to the client 1000 in step S4. Alternatively, the controller 1100 replaces the examination condition with the examination condition after the change. Alternatively, the controller 1100 replaces the examination condition inputted to the client 1000 in step S4 with the examination condition after the change.

(S7: Set Examination Condition)

The controller 1100 sets the examination condition inputted in step S4 or the examination condition changed in step S6 for the examination unit 1200. In other words, the controller 1100 changes the setting of the examination unit 1200 based on the concerned examination condition.

(S8: Perform Examination)

The examination unit 1200 performs examination of the patient's eye in response to an instruction from the user, for example. The acquired examination data is stored in a database (e.g., electronic medical record system or the like) in the medical institution. In addition, the examination data is sent to the management apparatus 11 together with the patient information and stored in the medical information storage apparatus 12.

[Usage Mode 2]

Figure 4:
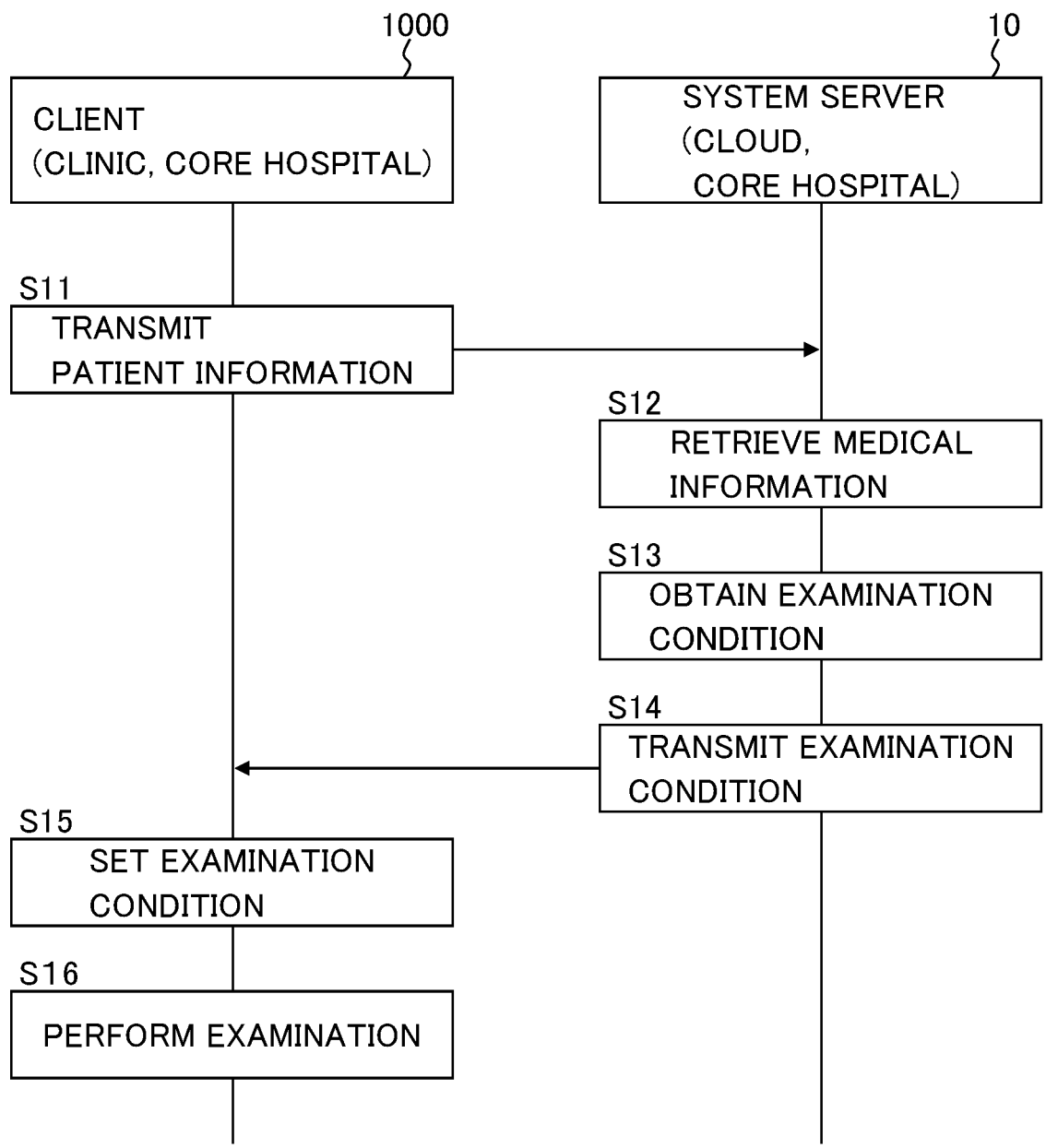
FIG. 4 is a sequence diagram showing an example of the usage mode of the ophthalmic examination support system of the embodiment.

The second usage mode is shown in FIG. 4.

(S11 to S14)

Steps S11 (transmit patient information), S12 (retrieve medical information), S13 (obtain examination condition) and S14 (transmit examination condition) are the same as steps S1, S2, S3 and S4, respectively.

(S15: Set Examination Condition)

In the present usage mode, the display of the examination condition by the client 1000 (S5) and the change of the examination condition by the user (S6) are not performed and the following processing is executed.

The communication unit 1400 of the client 1000 receives the examination condition transmitted from the management apparatus 11 in step S14 and sends it to the controller 1100. The controller 1100 changes the setting of the examination unit 1200 based on the examination condition.

(S16: Perform Examination)

Then, the examination is performed in the same manner as in step S8 of the first usage mode.

[Usage Mode 3]

Figure 5:
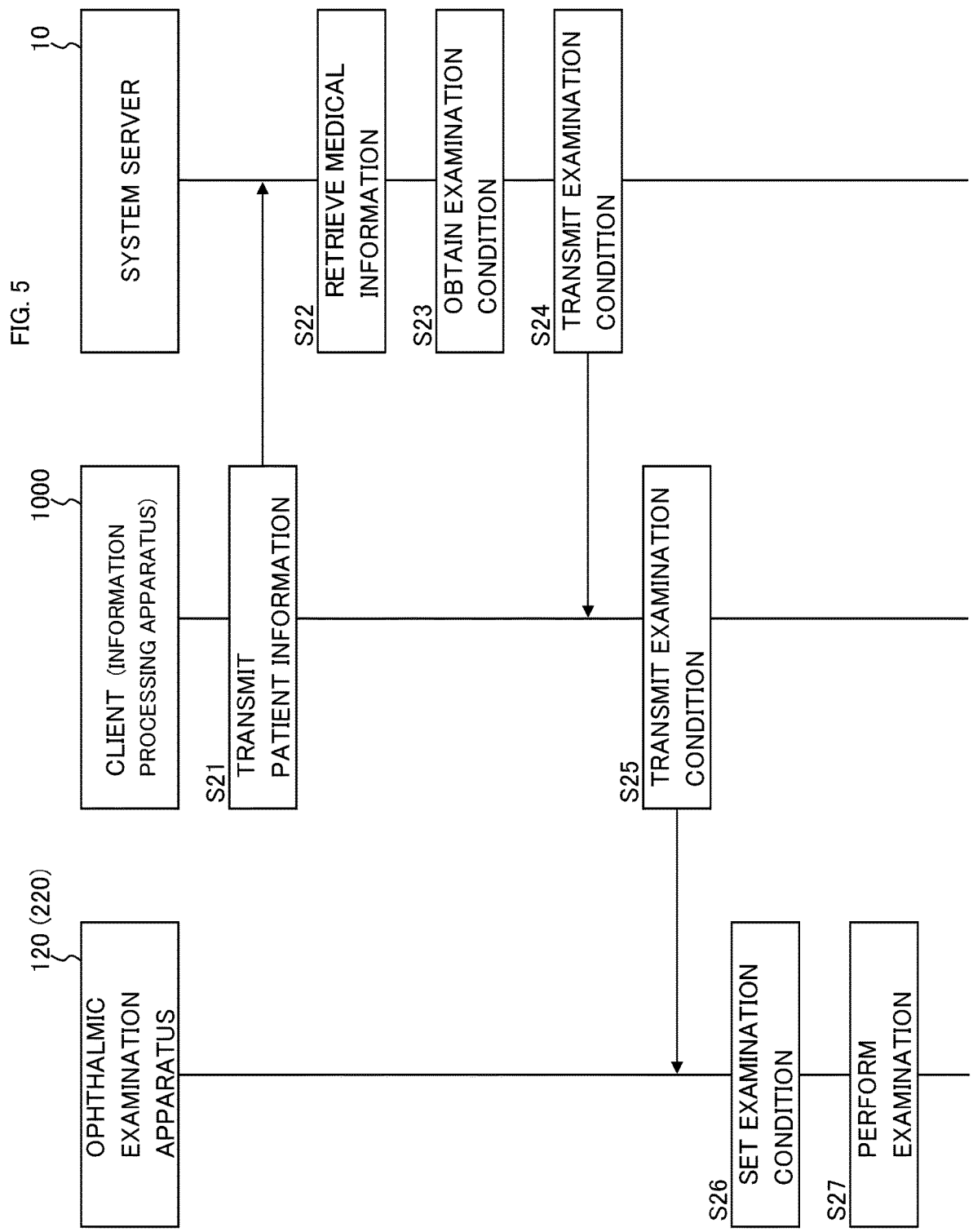
FIG. 5 is a sequence diagram showing an example of the usage mode of the ophthalmic examination support system of the embodiment.

The third usage mode is shown in FIG. 5. In the present usage mode, the client 1000 is the information processing apparatus 110 (or 210). The ophthalmic examination apparatus 120 (or 220) is connected to the client 1000.

(S21 to S24)

Steps S21 (transmit patient information), S22 (retrieve medical information), S23 (obtain examination condition) and S24 (transmit examination condition) are the same as steps S1, S2, S3 and S4, respectively.

(S25: Transmit Examination Condition)

The communication unit 1400 of the client 1000 receives the examination condition transmitted from the management apparatus 11 in step S24 and sends it to the controller 1100. The controller 1100 sends the examination condition to the ophthalmic examination apparatus 120 (or 220) by controlling the communication unit 116.

Before transmitting the examination condition, changes may be made. The examination condition is changed, for example, through the display of the examination condition as in the first usage mode.

(S26: Set Examination Condition)

The processor included in the ophthalmic examination apparatus 120 (or 220) changes the setting of the examination unit 1200 based on the examination condition inputted from the client 1000 (i.e., the information processing apparatus 110 (or 210)) in step S25.

(S27: Perform Examination)

The ophthalmic examination apparatus 120 (or 220) performs the examination in the same manner as in step S8 of the first usage mode.

[Usage Mode 4]

Figure 6:
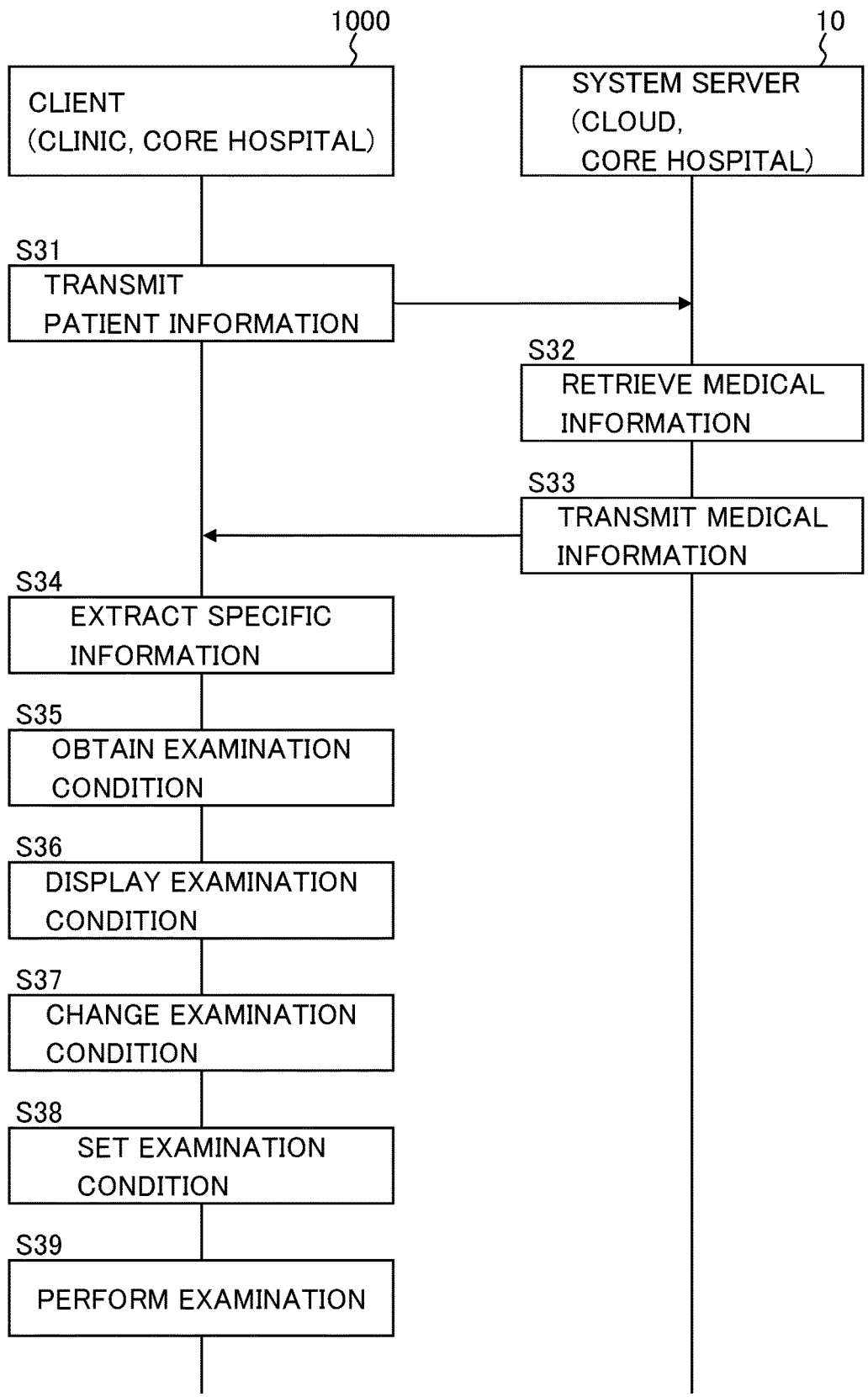
FIG. 6 is a sequence diagram showing an example of the usage mode of the ophthalmic examination support system of the embodiment.

In the first to third usage modes, the management apparatus 11 includes the association information storage unit 112, the examination condition obtaining unit 115, and the like. On the other hand, it is also possible for the client 1000 to include a storage device having the same function as the association information storage unit and a processor having the same function as the examination condition obtaining unit. In the case where such a configuration is applied, the fourth to sixth usage modes can be implemented. A fourth usage mode is shown in FIG. 6.

(S31, S32)

Steps S31 (transmit patient information) and S32 (retrieve medical information) are the same as steps S1 and S2 of the first usage mode, respectively.

(S33: Transmit Medical Information)

The controller 111 of the management apparatus 11 of the system server 10 controls the communication unit 116 to transmit the medical information retrieved by the retrieving unit 114 in step S32 to the client 1000 that is the transmission source of the patient information.

It should be noted that the transmission source of the patient information and the transmission destination of the medical information may be different. In that case, the transmission destination of the medical information is set in advance, or it is set each time using the client 1000 or the like.

(S34: Extract Specific Information)

The communication unit 1400 of the client 1000 receives the medical information transmitted from the management apparatus 11 in step S33 and sends it to the controller 1100. The processor that functions as the examination condition obtaining unit extracts specific information from the medical information. The specific information is information corresponding to medical information of a predetermined item included in the association information. The process of extracting the specific information from the medical information of the patient is executed in the same manner as the process executed by the examination condition obtaining unit 115 for extracting the medical information corresponding to the prescribed item from the medical information retrieved by the retrieving unit 114.

(S35: Obtain Examination Condition)

The processor that functions as the examination condition obtaining unit obtains the examination condition corresponding to the specific information extracted in step S34 from the association information stored in the storage device that functions as the association information storage unit. The examination condition obtained is sent to the controller 1100.

(S36: Display Examination Condition)

The controller 1100 displays the examination condition inputted in step S35 on the display 1310. This process is executed in the same manner as in step S5 of the first usage mode.

(S37 to S39)

Steps S37 (change examination condition), S38 (set examination condition) and S39 (perform examination) are the same as steps S6, S7 and S8 of the first usage mode, respectively.

[Usage Mode 5]

Figure 7:
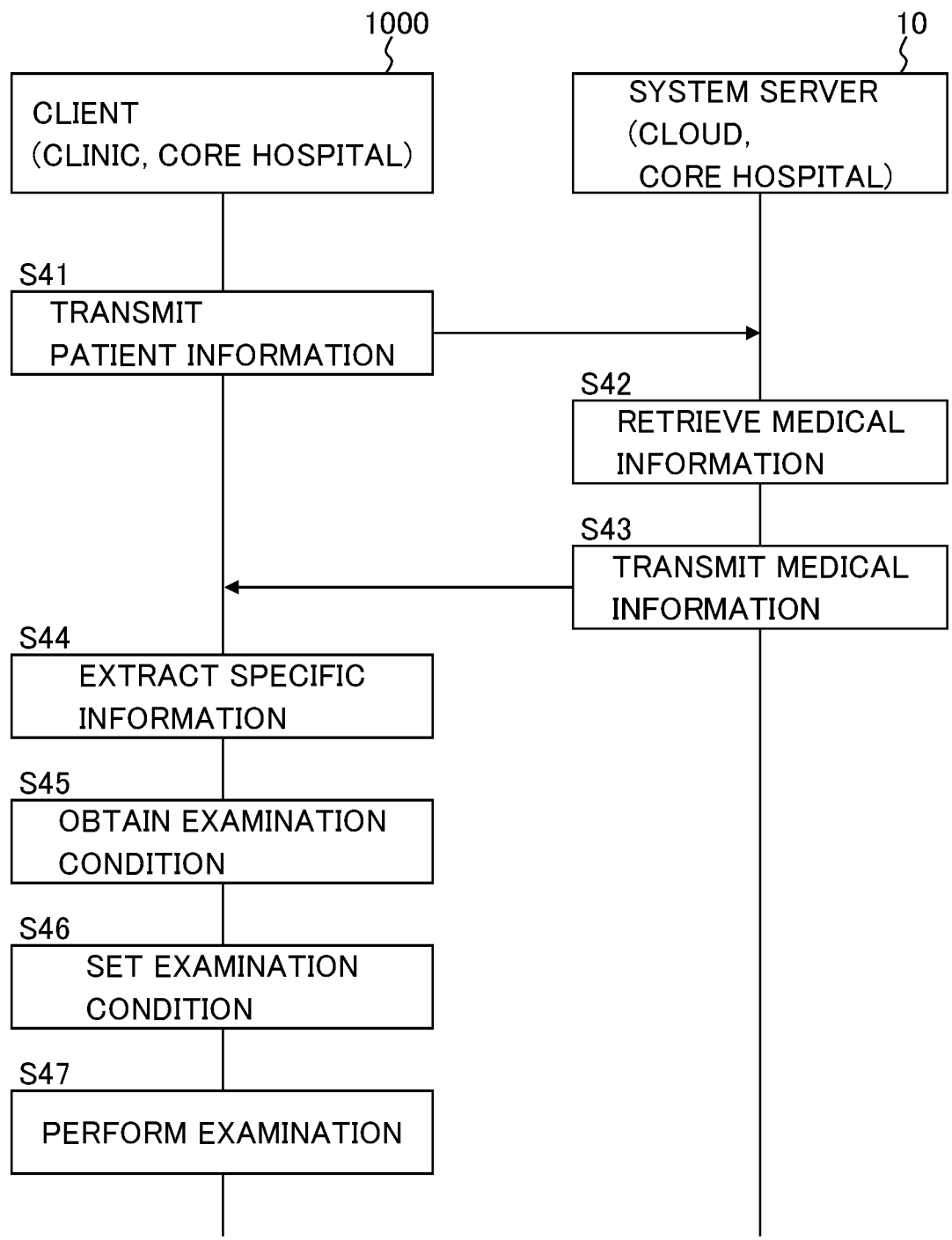
FIG. 7 is a sequence diagram showing an example of the usage mode of the ophthalmic examination support system of the embodiment.

The fifth usage mode is shown in FIG. 7.

(S41 to S45)

Step S41 (transmit patient information), S42 (retrieve medical information), S43 (transmit medical information), S44 (extract specific information) and S45 (obtain examination condition) are the same as steps S31, S32, S33, S34 and S35 in the fourth usage mode, respectively.

(S46: Set Examination Condition)

In the present usage mode, the display of the examination condition by the client 1000 (S36) and the change of the examination condition by the user (S37) are not performed, and the controller 1100 changes the setting of the examination unit 1200 based on the examination condition obtained in the step S45.

(S47: Perform Examination)

Then, the examination is performed in the same manner as in step S39 of the fourth usage mode.

[Usage Mode 6]

The sixth usage mode is shown in FIG. 8. In the present usage mode, like the third usage mode, the client 1000 is the information processing apparatus 110 (or 210), and the ophthalmic examination apparatus 120 (or 220) is connected to the client 1000.

(S51 to S55)

Steps S51 (transmit patient information), S52 (retrieve medical information), S53 (transmit medical information), S54 (extract specific information) and S55 (obtain examination condition) are the same as steps S31, S32, S33, S34 and S35.

(S56: Transmit Examination Condition)

By controlling the communication unit 116, the controller 1100 of the client 1000 sends the examination condition obtained in step S55 to the ophthalmic examination apparatus 120 (or 220).

Before transmitting the examination condition, changes may be made. The examination condition is changed, for example, through the display of the examination condition as in the first usage mode.

(S57: Set Examination Condition)

The processor included in the ophthalmic examination apparatus 120 (or 220) changes the setting of the examination unit 1200 based on the examination condition inputted from the client 1000 (e.g., the information processing apparatus 110 (or 210)) in step S56.

(S58: Perform Examination)

The ophthalmic examination apparatus 120 (or 220) performs the examination in the same manner as the step S39 of the fourth usage mode.

The usage modes described above are typical examples of usage modes that can be carried out using the ophthalmic examination support system according to the present embodiment, and other usage modes can also be employed.

[Actions and Effects]

The actions and effects of the ophthalmic examination support system according to the embodiment will be described.

The ophthalmic examination support system according to the embodiment includes a server (the system server 10) and a plurality of clients (1000). The server includes a medical information storage apparatus (12) configure to store medical information of each patient, and a management apparatus (11) configured to manage the medical information stored in the medical information storage apparatus. Each of the clients is capable of communicating with the management apparatus.

The ophthalmic examination support system according to the embodiment includes an association information storage unit and an examination condition obtaining unit. Each of the association information storage unit and the examination condition obtaining unit is arranged in an arbitrary location. For example, the association information storage unit is arranged in at least one of a server, one or more clients, and other locations. Alternatively, the association information storage unit may be distributed in at least two of the server, one or more clients, and other locations. Likewise, the examination condition obtaining unit may be arranged in at least one of a server, one or more clients, and other locations. Alternatively, the examination condition obtaining unit may be distributed in at least two of the server, one or more clients, and other locations.

The association information storage unit is configured to store, in advance, association information in which predetermined medical information items are associated with examination conditions of ophthalmic examinations. The examination condition obtaining unit is configured to receive medical information retrieved from the medical information storage apparatus by the management apparatus based on patient information sent from one of the plurality of clients, and to obtain, from the association information, an examination condition(s) corresponding to at least part of the received medical information.

The client includes a controller (1100) configured to execute control based on the examination condition obtained by the examination condition obtaining unit. The control executed by the controller may include arbitrary processing.

As the first example of the control, the controller can display the examination condition obtained by the examination condition obtaining unit on the display device (the display 1310).

In the second example of the control, the client includes an examination unit (1200) for performing an examination on the patient's eye. The controller can control the examination unit based on the examination condition obtained by the examination condition obtaining unit. In other words, the controller can set the examination condition obtained by the examination condition obtaining unit for the examination unit.

In the third example of the control, the client (the information processing apparatus 110 or 210) is capable of communicating with the ophthalmic examination apparatus (120 or 220) that performs an examination on the patient's eye. The controller can transmit the examination condition obtained by the examination condition obtaining unit to the ophthalmic examination apparatus. The ophthalmic examination apparatus is capable of performing an examination based on the examination condition inputted from the client.

As described above, the ophthalmic examination support system according to the embodiment is configured to acquire an appropriate examination condition corresponding to the medical information of a patient from the association information, and to provide the examination condition to the client installed in the clinic or the like. Therefore, an appropriate ophthalmic examination can be performed under appropriate conditions even in clinics or the like. This makes it possible to widely provide early detection methods and preventive medicine for eye diseases.

In the embodiment, the medical information stored in the medical information storage apparatus may include genetic information of patients. In addition, the association information may include first association information in which related genetic information of a predetermined disease is associated with examination conditions of ophthalmic examinations relating to the predetermined disease. Further, the examination condition obtaining unit may include a first obtaining unit capable of executing the following two processes. The first obtaining unit determines whether genetic information retrieved based on the patient information includes any of the related genetic information included in the first association information. In addition, the first obtaining unit obtains an examination condition(s) corresponding to related genetic information that is determined to be included in the retrieved genetic information, from the first association information.

According to this configuration, the examination condition can be determined from the risk of the onset of the predetermined disease obtained from the genetic information of the patient, and the determined examination condition can be provided to the client. Therefore, it is possible to widely provide early detection methods and preventive medicine for eye diseases that can be specified based on genes.

In the embodiment, the medical information stored in the medical information storage apparatus may include an image of a patient's eye. The association information may include second association information in which a plurality of pieces of feature information each indicating a morphological feature and/or a functional feature of eyes suffering from a predetermined disease is associated with examination conditions of ophthalmic examinations relating to the predetermined disease. In addition, the examination condition obtaining unit may include a second obtaining unit capable of executing the following two processes. The second obtaining unit analyzes an image retrieved based on the patient information to determine whether the retrieved image indicates any of morphological features and/or functional features included in the second association information. Furthermore, the second obtaining unit obtains an examination condition(s) corresponding to the feature information indicating the morphological feature(s) and/or the functional feature(s) determined to be indicated in the retrieved image, from the second association information. Note that the image in the present example may include an OCT image.

According to this configuration, it is possible to determine a morphological feature and/or a functional feature of eyes suffering from a predetermined disease based on an image of a patient's eye, and to provide an examination condition corresponding to the determined feature to the client. Therefore, it is possible to widely provide early detection methods and preventive medicine for eye diseases that can be specified based on an image of a patient's eye.

In the embodiment, the medical information stored in the medical information storage apparatus may include image analysis data obtained through analysis of an image of a patient's eye. The association information may include second association information in which a plurality of pieces of feature information each indicating a morphological feature and/or a functional feature of eyes suffering from a predetermined disease is associated with examination conditions of ophthalmic examinations relating to the predetermined disease. In addition, the examination condition obtaining unit may include a third obtaining unit capable of executing the following two processes. The third obtaining unit determines whether image analysis data retrieved based on the patient information corresponds to any of the feature information included in the second association information. Furthermore, the third obtaining unit obtains an examination condition(s) corresponding to the feature information determined to correspond to the retrieved image analysis data, from the second association information. Note that the image in the present example may include an OCT image.

According to this configuration, it is possible to determine a morphological feature and/or a functional feature of eyes suffering from a predetermined disease based on image analysis data of a patient's eye, and to provide an examination condition corresponding to the determined feature to the client. Therefore, it is possible to widely provide early detection methods and preventive medicine for eye diseases that can be specified based on an image of a patient's eye.

The ophthalmic examination support server (the system server 10) according to the embodiment will be described. The ophthalmic examination support server includes a medical information storage unit (the medical information storage apparatus 12), an association information storage unit (112), a communication unit (116), a retrieving unit (114), and an examination condition obtaining unit (115). The medical information storage unit is configured to store medical information on each patient. The association information storage unit is configured to store, in advance, association information in which association between predetermined medical information items and examination conditions of an ophthalmic examination is recorded. The communication unit is configured to receive patient information transmitted from one of a plurality of clients. The retrieving unit is configured to retrieve medical information from the medical information storage apparatus based on the patient information received. The examination condition obtaining unit is configured to obtain an examination condition corresponding to at least part of the retrieved medical information from the association information. The communication unit transmits the examination condition obtained to the client that has transmitted the patient information.

As described above, the ophthalmic examination support server of the present aspect is configured to acquire an appropriate examination condition corresponding to medical information of a patient from the association information, and to provide the examination condition to a client installed in a clinic or the like. Therefore, an appropriate ophthalmic examination can be performed under appropriate conditions even in clinics or the like. This makes it possible to widely provide early detection methods and preventive medicine for eye diseases.

The ophthalmic examination support device (the client 1000) according to the embodiment will be described. The ophthalmic examination support device includes a communication unit (1400) and a controller (1100). The communication unit is configured to transmit patient information to a server that manages medical information on each patient and stores, in advance, association information in which association between predetermined medical information items and examination conditions of an ophthalmic examination is recorded. Further, the communication unit is configured to receive an examination condition obtained from the association information based on the patient information from the server. The controller is configured to execute control based on the examination condition received.

In this way, the ophthalmic examination support device according to the embodiment, which is installed in a clinic or the like, can receive appropriate examination conditions obtained from the association information according to the medical information on the patient, from the server. In addition, based on the examination conditions received, the ophthalmic examination support device can execute control. Therefore, an appropriate ophthalmic examination can be performed under appropriate conditions even in clinics or the like. This makes it possible to widely provide early detection methods and preventive medicine for eye diseases.

A computer program for realizing at least part of the processing included in the embodiment can be stored in a non-transitory computer readable recording medium. Examples of the recording medium include a semiconductor memory, an optical disk, a magneto-optical disk, a magnetic storage medium, and the like. It is also possible to send and/or receive this computer program via a network such as the Internet or LAN.

The configuration described above is only an example of the embodiment. Those who intend to implement the present invention can apply any change (e.g., omission, substitution, addition, or the like) in an arbitrary manner within the scope of the gist of the present invention.

The invention claimed is:

1. An ophthalmic examination support system comprising:
   a server that comprises a medical information storage apparatus configured to store medical information on each patient, and a management apparatus configured to manage the medical information stored in the medical information storage apparatus; and
   a plurality of clients each of which is capable of communicating with the management apparatus,
   wherein the ophthalmic examination support system comprises:
   an association information storage unit configured to store, in advance, association information in which association between predetermined medical information items and examination conditions of an ophthalmic examination is recorded; and
   an examination condition obtaining unit configured to receive medical information retrieved from the medical information storage apparatus by the management apparatus based on patient information transmitted from one of the plurality of clients, and to obtain an examination condition corresponding to at least part of the received medical information from the association information,
   wherein the one of the plurality of clients comprises a controller configured to execute control based on the examination condition obtained by the examination condition obtaining unit,
   the medical information stored in the medical information storage apparatus comprises genetic information of a patient,
   the association information comprises first association information in which association between related genetic information of predetermined disease and examination conditions of an ophthalmic examination relating to the predetermined disease is recorded, and
   the examination condition obtaining unit comprises a first obtaining unit configured to execute a first process of determining whether genetic information retrieved based on the patient information comprises any of the related genetic information comprised in the first association information, and a second process of obtaining an examination condition corresponding to related genetic information that has been determined to be comprised in the retrieved genetic information from the first association information,
   wherein the first obtaining unit executes a process of determining a risk of a specific disease from the genetic information retrieved based on the patient information in the first process, and a process of obtaining an examination condition from the risk of the specific disease in the second process.

2. The ophthalmic examination support system of claim 1, wherein the controller controls a display device to display the examination condition obtained by the examination condition obtaining unit.

3. The ophthalmic examination support system of claim 1,
   wherein the one of the plurality of clients comprises an examination unit for performing examination of an eye of the patient, and
   the controller controls the examination unit based on the examination condition obtained by the examination condition obtaining unit.

4. The ophthalmic examination support system of claim 1,
   wherein the one of the plurality of clients is capable of communicating with an ophthalmic examination apparatus for performing examination of an eye of the patient, and
   the controller transmits the examination condition obtained by the examination condition obtaining unit to the ophthalmic examination apparatus.

5. The ophthalmic examination support system of claim 1,
   wherein the medical information stored in the medical information storage apparatus comprises an image of an eye of the patient,
   the association information comprises second association information in which association between feature information indicating morphological features and/or functional features of eyes suffering from predetermined disease and examination conditions of an ophthalmic examination relating to the predetermined disease is recorded, and
   the examination condition obtaining unit comprises a second obtaining unit configured to execute a process of analyzing an image retrieved based on the patient information to determine whether the retrieved image indicates any of the morphological features and/or the functional features comprised in the second association information, and a process of obtaining an examination condition corresponding to feature information indicating a morphological feature and/or a functional feature determined to be indicated in the retrieved image from the second association information.

6. The ophthalmic examination support system of claim 1,
   wherein the medical information stored in the medical information storage apparatus comprises image analysis data obtained through analysis of an image of an eye of the patient,
   the association information comprises second association information in which association between feature information indicating morphological features and/or functional features of eyes suffering from predetermined disease and examination conditions of an ophthalmic examination relating to the predetermined disease is recorded, and
   the examination condition obtaining unit comprises a third obtaining unit configured to execute a process of determining whether image analysis data retrieved based on the patient information corresponds to any of the feature information comprised in the second association information, and a process of obtaining an examination condition corresponding to feature information determined to correspond to the retrieved image analysis data from the second association information.

7. The ophthalmic examination support system of claim 5, wherein the image comprises an OCT image acquired using optical coherence tomography.

8. The ophthalmic examination support system of claim 6, wherein the image comprises an OCT image acquired using optical coherence tomography.

9. The ophthalmic examination support system of claim 2, wherein the one of the plurality of clients comprises an examination unit for performing examination of an eye of the patient, and
the controller controls the examination unit based on the examination condition obtained by the examination condition obtaining unit.

10. The ophthalmic examination support system of claim 2,
wherein the one of the plurality of clients is capable of communicating with an ophthalmic examination apparatus for performing examination of an eye of the patient, and
the controller transmits the examination condition obtained by the examination condition obtaining unit to the ophthalmic examination apparatus.

11. The ophthalmic examination support system of claim 2,
wherein the medical information stored in the medical information storage apparatus comprises image analysis data obtained through analysis of an image of an eye of the patient,
the association information comprises second association information in which association between feature information indicating morphological features and/or functional features of eyes suffering from predetermined disease and examination conditions of an ophthalmic examination relating to the predetermined disease is recorded, and
the examination condition obtaining unit comprises a third obtaining unit configured to execute a process of determining whether image analysis data retrieved based on the patient information corresponds to any of the feature information comprised in the second association information, and a process of obtaining an examination condition corresponding to feature information determined to correspond to the retrieved image analysis data from the second association information.

12. The ophthalmic examination support system of claim 2,
wherein the medical information stored in the medical information storage apparatus comprises an image of an eye of the patient,
the association information comprises second association information in which association between feature information indicating morphological features and/or functional features of eyes suffering from predetermined disease and examination conditions of an ophthalmic examination relating to the predetermined disease is recorded, and
the examination condition obtaining unit comprises a second obtaining unit configured to execute a process of analyzing an image retrieved based on the patient information to determine whether the retrieved image indicates any of the morphological features and/or the functional features comprised in the second association information, and a process of obtaining an examination condition corresponding to feature information indicating a morphological feature and/or a functional feature determined to be indicated in the retrieved image from the second association information.

13. The ophthalmic examination support system of claim 3,
wherein the one of the plurality of clients is capable of communicating with an ophthalmic examination apparatus for performing examination of the eye of the patient, and
the controller transmits the examination condition obtained by the examination condition obtaining unit to the ophthalmic examination apparatus.

14. The ophthalmic examination support system of claim 3,
wherein the medical information stored in the medical information storage apparatus comprises an image of the eye of the patient,
the association information comprises second association information in which association between feature information indicating morphological features and/or functional features of eyes suffering from predetermined disease and examination conditions of an ophthalmic examination relating to the predetermined disease is recorded, and
the examination condition obtaining unit comprises a second obtaining unit configured to execute a process of analyzing an image retrieved based on the patient information to determine whether the retrieved image indicates any of the morphological features and/or the functional features comprised in the second association information, and a process of obtaining an examination condition corresponding to feature information indicating a morphological feature and/or a functional feature determined to be indicated in the retrieved image from the second association information.

15. An ophthalmic examination support server comprising:
a medical information storage unit configured to store medical information on each patient;
an association information storage unit configured to store, in advance, association information in which association between predetermined medical information items and examination conditions of an ophthalmic examination is recorded;
a communication unit configured to receive patient information transmitted from one of a plurality of clients;
a retrieving unit configured to retrieve medical information from the medical information storage unit based on the patient information received; and
an examination condition obtaining unit configured to obtain an examination condition corresponding to at least part of the retrieved medical information from the association information,
wherein the communication unit transmits the examination condition obtained by the examination condition obtaining unit to the one of the plurality of clients,
the medical information stored in the medical information storage unit comprises genetic information of a patient,
the association information comprises first association information in which association between related genetic information of predetermined disease and examination conditions of an ophthalmic examination relating to the predetermined disease is recorded, and
the examination condition obtaining unit comprises a first obtaining unit configured to execute a first process of determining whether genetic information retrieved based on the patient information comprises any of the related genetic information comprised in the first association information, and a second process of obtaining an examination condition corresponding to related genetic information that has been determined to be comprised in the retrieved genetic information from the first association information, wherein the first obtaining unit executes a process of determining a risk of a specific disease from the genetic information retrieved based on the patient information in the first process, and a process of obtaining an examination condition from the risk of the specific disease in the second process.

16. An ophthalmic examination support device comprising:
- a communication unit configured to transmit patient information to a server that manages medical information on each patient and stores, in advance, association information in which association between predetermined medical information items and examination conditions of an ophthalmic examination is recorded, and receive an examination condition obtained from the association information based on the patient information from the server; and
- a controller configured to execute control based on the examination condition received, wherein the medical information comprises genetic information of a patient, the association information comprises first association information in which association between related genetic information of predetermined disease and examination conditions of an ophthalmic examination relating to the predetermined disease is recorded, and wherein the ophthalmic examination support device is configured to receive the examination condition from an examination condition obtaining unit comprising a first obtaining unit configured to execute a first process of determining whether genetic information retrieved based on the patient information comprises any of the related genetic information comprised in the first association information, and a second process of obtaining an examination condition corresponding to related genetic information that has been determined to be comprised in the retrieved genetic information from the first association information, wherein the first obtaining unit executes a process of determining a risk of a specific disease from the genetic information retrieved based on the patient information in the first process, and a process of obtaining an examination condition from the risk of the specific disease in the second process.

* * * * *